(12) United States Patent
Wang et al.

(10) Patent No.: US 6,590,102 B1
(45) Date of Patent: *Jul. 8, 2003

(54) PROCESS FOR PRODUCING PIPERIDINECARBINOLS

(75) Inventors: Shu-zhong Wang, Yokohama (JP); Takashi Okazoe, Yokohama (JP); Yasushi Matsumura, Yokohama (JP); Nobuaki Mori, Ichihara (JP); Jiro Nishino, Ichihara (JP); Kazuhiro Ookura, Ichihara (JP)

(73) Assignee: Asahi Glass Company Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/721,762

(22) Filed: Nov. 27, 2000

Related U.S. Application Data

(63) Continuation of application No. 08/835,646, filed on Apr. 11, 1997, now Pat. No. 6,197,960.

(30) Foreign Application Priority Data

Apr. 15, 1996 (JP) .................................................. 8-92791

(51) Int. Cl.[7] ...................... C07D 211/40; C07E 255/17
(52) U.S. Cl. ........................ 546/220; 546/210; 558/406
(58) Field of Search ............................... 546/210, 220; 558/406

(56) References Cited

U.S. PATENT DOCUMENTS

| | | | |
|---|---|---|---|
| 3,912,743 A | 10/1975 | Christensen et al. | 546/210 |
| 4,007,196 A | 2/1977 | Christensen et al. | 546/210 |
| 4,188,396 A * | 2/1980 | Haas et al. | 546/239 |
| 4,593,036 A | 6/1986 | Lassen et al. | 546/210 |
| 4,861,893 A | 8/1989 | Borrett | 546/210 |
| 4,902,801 A | 2/1990 | Faruk et al. | 546/220 |
| 5,019,582 A | 5/1991 | Drejer et al. | 514/321 |
| 5,227,379 A | 7/1993 | Jakobsen et al. | 514/228 |
| 5,258,517 A | 11/1993 | Zepp et al. | 546/240 |
| 5,672,612 A | 9/1997 | Ronsen et al. | 514/338 |
| 5,948,914 A * | 9/1999 | Sugi et al. | 546/240 |

FOREIGN PATENT DOCUMENTS

| | | |
|---|---|---|
| EP | 0 190 496 A2 | 8/1986 |
| EP | 0 374 675 A2 | 6/1990 |
| EP | 0 812 827 A1 | 12/1997 |
| ES | 9600369 | 2/1996 |
| ES | 9600819 | 4/1996 |
| JP | 6-96551 | 11/1994 |
| WO | WO 94/21609 | 9/1994 |

OTHER PUBLICATIONS

Ahlwalia et al. "A convenient one–pot synthesis of 1,3–dimethyl–2,4–dioxo–1,2,3,4–tetrahydro–10H–pyrimido[5,4–b][1,4]benzothiazines" CA 121:57453 (1994).*

Mukhopadhyay et al, "Synthesis of cheaper resolving agent, N–alkyl glucamines: Some aspects of process development", Pascal No., 99–0298009, 1999.

Lang et al, "Hydrogenation De L'O–Nitrophenol et du maleate de sodium sous pression en phase liquide", Pascal No. 80–0306187, 1980.

Kukharev et al, "Hydrogenation of 3,4–pyridylidene aminoethanols and flotation properties of the products of their reduction". SCISEARCH NU28.

Hudlicky, "Chemistry of Organic Fluorine Compounds", Wiley & sons, p. 170–179, 1976.

Moos et al, "Codeine Analogues. Synthesis of Spiro [benzofuran–3(2H), 4'–piperidines] and Octahydro–1H–benzofuro[3,2–e]isoquinolines", J. Org. Chem., p. 5064–5074, 1981, vol. 46.

Okazaki et al, "Hydrogenation pathway of quinolines over Raney nickel and Ru/C", JICST Accession No. 90A0911348.

Privette et al, "Polyhydric alcohols", CAPLUS 69:106011.

Plati et al, "Pyridindene Derivatives. III. Synthesis from Arecoline", J. Org. Chem., vol. 22, p. 261–265, Mar. 1957.

(List continued on next page.)

*Primary Examiner*—Ceila Chang
(74) *Attorney, Agent, or Firm*—Oblon, Spivak, McClelland, Maier & Neustadt, P.C.

(57) ABSTRACT

A process for producing a piperidinecarbinol represented by the general formula (2), which comprises reducing the trans isomer of a compound represented by the general formula (1):

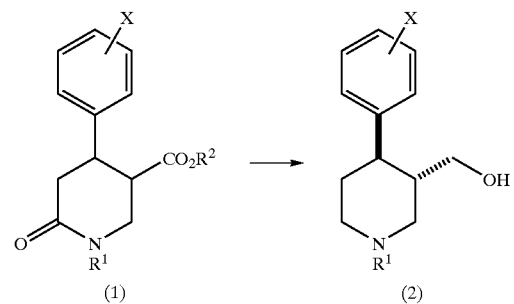

wherein $R^1$ is a hydrogen atom, a lower alkyl group or an aralkyl group, $R^2$ is a hydrogen atom, a lower alkyl group, an aryl group or an aralkyl group, and X is a hydrogen atom, a halogen atom, an alkyl group, an aryl group, an aralkyl group, an alkoxy group, a dialkylamino group, an alkylthio group, an arylthio group or $C_mF_{2m+1}$— wherein m is an integer of from 1 to 20.

18 Claims, No Drawings

OTHER PUBLICATIONS

Jutz et al, "Uber die vilsmeier–formylierung von ungesaettigten kohlenwasserstoffen", Chem. Ber., vol. 99, p. 2479–2490.

Christensen et al. "On the formation of the 1–AZA–[3.1.1]–bicycloheptane ring system", Tetrahedron Letters, vol. 24, No. 46, p. 5151–5152, 1983.

Koelsch et al, "A synthesis of 4–phenylpiperidines", J. Chem. Soc., vol. 65, 1943, p. 2459–2460.

Weller et al, "Synthesis of 4a–Aryldecahydroisoquinolines. Functionality in the carbocyclic ring", The Journal of Organic Chemistry, vol. 42, No. 9, p. 1485–1495, 1977.

Lapuyade et al, "Derives alkyles et aryles de l'acide nipecotique: synthese et appreciation de l'activite inhibitrice de la capture du GABA en fonction de parametres conformationnels et de biodisponibilite", Eur. J. Med. Chem., vol. 22, No. 5, p. 383–391, 1987.

De Koning et al, "Hydrogenolysis of aryl halides in the presence of raney nickel in alkaline medium", Organic Preparations and Procedures Int., vol. 7, No. 1, p. 31–34, 1975.

* cited by examiner

PROCESS FOR PRODUCING PIPERIDINECARBINOLS

This is a application is a continuation of Ser. No. 08/835,646 filed Apr. 11, 1997 now U.S. Pat. No. 6,197,960.

BACKGROUND OF THE INVENTION

1. Field of the Invention

The present invention relates to a process for producing piperidinecarbinols useful as intermediates for synthesizing medicines, particularly to a process for producing trans-4-(p-fluorophenyl)-1-methyl-3-piperidinecarbinol, which is an important intermediate in synthesis of paroxetine, which is useful as an antidepressant or a therapeutic agent for Parkinson's disease. The present invention also relates to intermediates useful for producing the piperidinecarbinols and a process for producing the intermediates.

2. Discussion of Background

Conventionally known processes for producing 4-aryl-3-piperidinecarbinols useful for synthesizing medicines are the following four processes (a) to (d).

(a) A process which comprises reducing an 4-aryl-3-piperidinecarboxylic acid ester represented by the following general formula (4) with lithium aluminum hydride (U.S. Pat. No. 3,912,743):

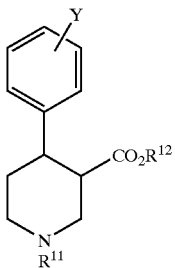

(4)

wherein $R^{11}$ is a lower alkyl group or an aryl group, $R^{12}$ is a lower alkyl-group, and Y is a hydrogen atom, a halogen atom, a methoxy group or a mercapto group.

A compound represented by the general formula (4) is synthesized by a process which comprises reacting an aryl Grignard reagent with arecoline (J. Org. Chem., 1957, 22, 201) or by a process which comprises a series of steps including reaction of an aryl Grignard reagent with a nicotinic acid ester and reductive hydrogenation of an 4-aryl-1-methyl-3-alkoxycarbonylpyridinium salt with a platinum catalyst (U.S. Pat. No. 4,861,893).

However, the former process has a problem of using expensive and irritating arecoline as a starting material. In addition, since the conjugate addition of a Grignard reagent to arecoline competes with the 1,2-addition, a mixture of the products of these two reactions is produced in the process, and therefore the desired product is very hard to isolate and generally obtainable in a low yield. The latter process is not practical in respect of the production cost and efficiency because it requires many steps.

(b) A process which comprises reducing an 4-aryl-2,6-dioxo-3-piperidinecarboxylic acid ester represented by the general formula (5) with lithium aluminum hydride (Japanese Examined Patent Publication JP-B-6-96551):

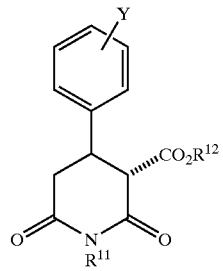

(5)

wherein $R^{11}$ is a hydrogen atom, a lower alkyl group or an aralkyl group, $R^{12}$ is a lower alkyl group, and Y is a hydrogen atom, a halogen atom, a lower alkyl group, an aralkyloxy group, a trifluoroalkyl group, a hydroxyl group, a methoxy group or a mercapto group.

A compound represented by the general formula (5) is synthesized by a process which comprises conjugate addition of a N-substituted amidomalonic acid ester to a cinnamic acid derivative, a process which comprises conjugate addition of an amidomalonic acid ester to a cinnamic acid derivative and subsequent N-alkylation (Japanese Examined Patent Publication JP-B-6-96551) or a process which comprises conjugate addition of a malonic acid ester to cinnamamide (EP 0374675).

However, the first two processes have problems that an amidomalonic acid ester as the starting material tends to undergo disproportionation and thus is difficult to produce, and is generally so expensive as to be hardly available, and that a compound represented by the formula (5) is not reactive enough to be readily reduced. The last process uses a free amine as the starting material for synthesis of cinnamamide, and prevention of the bad smell of the amine from leaking out inevitably adds to manufacturing costs.

(c) A process which comprises reducing an 4-aryl-3-hydroxymehtyl-1-alkylpyridinium salt represented by the general formula (6) directly or stepwise (U.S. Pat. No. 4,861,893):

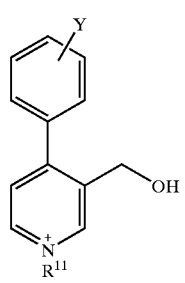

(6)

wherein $R^{11}$ is a hydrogen atom or a lower alkyl group, and Y is a hydrogen atom, a halogen atom, a lower alkyl group, an aralkyloxy group, a trifluoroalkyl group, a hydroxyl group, a methoxy group or a mercapto group.

A compound represented by the general formula (6) is synthesized by a process which comprises a series of conversions such as reduction of an 4-arylnicotinic aldehyde prepared by the method of Jutz et al. (Chem. Ber., 1966, 99, 2479) into a hydroxylmethylpyridine derivative and subsequent N-alkylation. However, the process (c) which involves the series of conversions requires so many steps that it is problematic in the production efficiency and practicability.

(d) A process which comprises reducing an 4-aryl-3-hydroxymehtyl-1,2,3,6-tetrahydropyridine represented by the general formula (7) (Tetrahedron Lett., 1983, 24, 5151):

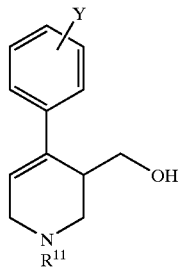
(7)

wherein $R^{11}$ is a lower alkyl group, and Y is a hydrogen atom or a halogen atom.

A compound represented by the general formula (7) is synthesized by a process which comprises ene reaction of an 4-aryl-1-alkyl-1,4,5,6-tetrahydropyridine and formaldehyde (U.S. Pat. No. 4,007,196), or by a process which comprises reacting a 2-propenylaryl derivative with methylamine and formaldehyde (U.S. Pat. No. 4,593,036). However, because in this process, a highly neurotoxic 4-aryl-1-alkyl-1,4,5,6-tetrahydropyridine is unavoidable, this process is actually impractical in respect of industrial safety.

On the other hand, as processes for producing 4-aryl-6-oxo-3-piperidinecarboxylic acid derivatives, which will be described later, the following two processes (e) and (f) which comprise reduction of the cyano group of a 2-cyano-3-arylglutaric acid derivative to an amino group and subsequent cyclization have been known.

(e) A process reported by Koelsch which comprises hydrogenating diethyl 2-cyano-3-phenylglutarate with a Raney nickel catalyst (J. Am. Chem. Soc., 1943, 2459).

(f) A process reported by Rapoport et al. which comprises hydrogenating diethyl 2-cyano-3-(m-methoxyphenyl) glutarate with a platinum oxide catalyst (J. Org. Chem., 1977, 1485).

The process (e) uses a very high hydrogen pressure around 140 atm and therefore is industrially far from practicable. Besides, the process (e) is not suitable for production of an 4-aryl-6-oxo-3-piperidinecarboxylic acid having a halogen atom on the aryl group, because under such a high pressure, the halogen atom on a benzene ring is also reduced. The process (f) is not advantageous in respect of production costs and efficiency because the reduction of the cyano group and cyclization are conducted in two steps.

SUMMARY OF THE INVENTION

To solve the above-mentioned problems with the conventional processes, the present inventors have found a novel process for producing a piperidinecarbinol represented by the following general formula (2) which uses an 4-aryl-6-oxo-3-piperidinecarboxylic acid represented by the general formula (1) as an important intermediate. The present invention provides the said production process, a novel 4-aryl-6-oxo-3-piperidinecarboxylic acid derivative and a process for producing the derivative. Namely, the present invention provides;

a process for producing a piperidinecarbinol represented by.the general formula (2), which comprises reducing the trans isomer of a compound represented by the general formula (1):

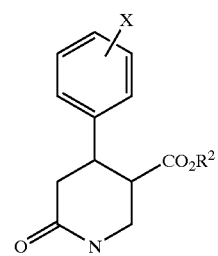
(1)

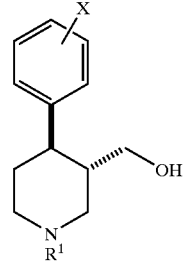
(2)

wherein $R^1$ is a hydrogen atom, a lower alkyl group or an aralkyl group, $R^2$ is a hydrogen atom, a lower alkyl group, an aryl group or an aralkyl group, and X is a hydrogen atom, a halogen atom, an alkyl group, an aryl group, an aralkyl group, an alkoxy group, a dialkylamino group, an alkylthio group, an arylthio group or $C_mF_{2m+1}$— wherein m is an integer of from 1 to 20;

a compound represented by the general formula (1'):

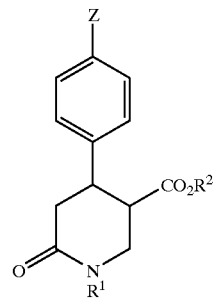
(1')

wherein $R^1$ is a hydrogen atom, a lower alkyl group or an aralkyl group, $R^2$ is a hydrogen atom, a lower alkyl group, an aryl group or an aralkyl group, and Z is a halogen atom;

a process for producing a compound represented by the general formula (1') wherein $R^1$ is a hydrogen atom, which comprises reducing of the cyano group of a cyanoglutaric acid derivative represented by the general formula (3) and simultaneous intramolecular cyclization of the cyanoglutaric acid derivative:

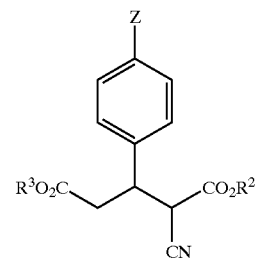
(3)

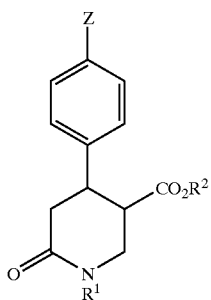

(1')

wherein each of $R^2$ and $R^3$ is a hydrogen atom, a lower alkyl group, an aryl group or an aralkyl group, and Z is a halogen atom;

a cyanoglutaric acid derivative represented by the general formula (3):

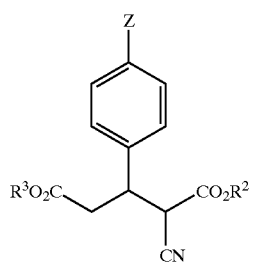

(3)

wherein each of $R^2$ and $R^3$ is a hydrogen atom, a lower alkyl group, an aryl group or an aralkyl group, and Z is a halogen atom;

a process for producing a piperidinecarbinol represented by the general formula (2) wherein $R^1$ is a lower alkyl group or an aralkyl group, which comprises converting $R^1$ of a piperidinecarbinol represented by the general formula (2) wherein $R^1$ is a hydrogen atom into a lower alkyl group or an aralkyl group:

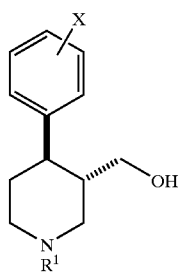

(2)

wherein X is a hydrogen atom, a halogen atom, an alkyl group, an aryl group, an aralkyl group, an alkoxy group, a dialkylamino group, an alkylthio group, an arylthio group or $C_mF_{2m+1}$— wherein m is an integer of from 1 to 20; and a process for producing trans-4-(p-fluorophenyl)-1-methyl-3-piperidinecarbinol, which comprises the following sequence of steps (i) to (v):

(i) a step of conjugately adding a cyanoacetic acid ester to a p-fluorocinnamic acid ester to prepare a 2-cyano-3-(p-fluorophenyl)glutaric acid diester;

(ii) a step of hydrogenating the 2-cyano-3-(p-fluorophenyl)glutaric acid diester in the presence of a metallic catalyst to prepare a cis/trans mixture of a 4-(p-fluorophenyl)-6-oxo-3-piperidinecarboxylic acid ester;

(iii) a step of treating the cis/trans mixture with a base or an acid to prepare a trans-4-(p-fluorophenyl)-6-oxo-3-piperidinecarboxylic acid ester;

(iv) a step of reducing the trans-4-(p-fluorophenyl)-6-oxo-3-piperidinecarboxylic acid ester to trans-4-(p-fluorophenyl)-3-piperidinecarbinol; and (v) a step of reacting the trans-4-(p-fluorophenyl)-3-piperidinecarbinol with formaldehyde or paraformaldehyde under a reductive atmosphere to prepare trans-4-(p-fluorophenyl)-1-methyl-3-piperidinecarbinol.

DETAILED DESCRIPTION OF THE PREFERRED EMBODIMENTS

Hereinabove and hereinafter, "lower" for an organic group means from 1 to 6 carbon atoms. Preferable lower organic groups are those with a carbon number of from 1 to 4. As "an alkyl group", those of lower class, i.e. "lower alkyl groups" are preferable. As "a lower alkyl group", those with a carbon number of from 1 to 2, i.e. a methyl group and an ethyl group are particularly preferable. Suitable "lower alkyl groups" are, for example, a methyl group, an ethyl group, a propyl group, an isopropyl group, a butyl group, an isobutyl group, a t-butyl group, a pentyl group, an isoamyl group, a hexyl group and a 1,1,2-trimethylpropyl group.

As "an alkoxy group", lower alkoxy groups are preferred, and suitable examples of the alkoxy group include a methoxy group, an ethoxy group, an isopropoxy group and a t-butoxy group. As "a dialkylamino group", lower alkylamino groups are preferred, and suitable examples of the dialkylamino group are a dimethylamino group and a diethylamino group. As "an alkylthio group", lower alkylthio groups are preferred, and its suitable examples are a methylthio group, an ethylthio group, a propylthio group and a butylthio group.

Hereinabove and hereinafter, "a halogen atom" means a fluorine atom, a chlorine atom, a bromine atom or an iodine atom. "An aryl group" means a monovalent aromatic hydrocarbon group, and a phenyl group or its derivative is preferred. Its suitable examples are a phenyl group, a tolyl group, a methoxyphenyl group, a p-halophenyl group and the like. "An aralkyl group" means an alkyl group substituted with an aryl group in which the alkyl group preferably has a carbon number of at most 4. Its suitable examples are a benzyl group, a benzhydryl group, a trityl group, a phenethyl group and the like. "An arylthio group" means a thio group substituted with an aryl group, and its suitable examples are a phenylthio group, a tolylthio group and the like.

Among the compounds represented by the general formula (1) [hereinafter referred to as compounds (1)] preferred are those wherein $R^2$ is a hydrogen atom or a lower alkyl group, and X is a halogen atom at the p-position. More preferred compounds (1) are those wherein $R^1$ is a hydrogen atom, a methyl group or a benzyl group, $R^2$ is a methyl group or an ethyl group, and X is a fluorine atom at the p-position.

A piperidinecarbinol represented by the general formula (2) [hereinafter referred to as a compound (2)], as is evident from its general formula, is a trans isomer in which the benzene ring and the carbinol group are in positions trans to each other. The trans isomer is particularly useful as an intermediate for a medicine. To prepare such a compound (2), the compound (1) has to be a trans isomer like the compound (2). A compound (1) is obtained in the form of a cis/trans mixture by the process for producing a compound (1) which is described later. Therefore, when the cis/trans mixture of a compound (1) prepared by this process is used for preparation of a compound (2), it is necessary to obtain the trans isomer only from the cis/trans mixture. The trans isomer is preferably obtained by the process which is described later.

The process for producing a compound (1) which is described later gives a compound (1) wherein $R^1$ is a hydrogen atom. Therefore, when a compound (1) wherein $R^1$ is a hydrogen atom prepared by this process is used for preparing a compound (2) wherein $R^1$ is a different substituent, $R^1$ of the compound (1) is converted to a substituent other than a hydrogen atom before preparation of the compound (2), or preparation of another compound (2) wherein $R^1$ is a hydrogen atom is followed by conversion of $R^1$ to a substituent other than a hydrogen atom.

Among the compounds (1), those wherein X is a halogen atom at the p-position of the phenyl group, namely, compounds represented by the general formula (1') [hereinafter referred to as compounds (1')] are novel and preferred. Among the compounds (1'), preferred are those wherein $R^2$ is a hydrogen atom or a lower alkyl group. More preferred are compounds (1') wherein $R^1$ is a hydrogen atom, a methyl group or a benzyl group, $R^2$ is a methyl group or an ethyl group, and Z is a fluorine atom.

Specific compounds preferred as compounds (1) and (1') are as follows. As the following alkyl esters, methyl esters and ethyl esters are preferred:

alkyl esters of trans-4-(p-fluorophenyl)-6-oxo-3-piperidinecarboxylic acid, alkyl esters of trans-4-(p-fluorophenyl)-1-methyl-6-oxo-3-piperidinecarboxylic acid, and alkyl esters of trans-1-benzyl-4-(p-fluorophenyl)-6-oxo-3-piperidinecarboxylic acid.

As described above, processes for producing an 4-aryl-6-oxo-3-piperidinecarboxylic acid derivative which comprises reduction of the cyano group of a 2-cyano-3-arylglutaric acid derivative to an amino group and subsequent cyclization has been basically known. However, these processes were not known to be applicable to a 2-cyano-3-(haloaryl)glutaric acid derivative having a halogen atom on the aryl group, and, if applied, are not expected to give the desired product in a satisfactory yield by itself. The cyanoglutaric acid derivatives represented by the formula (3) [hereinafter referred to as compounds (3)] are novel compounds. In the compounds (3), $R^3$ is preferably a hydrogen atom or a lower alkyl group, particularly preferably a methyl group or an ethyl group, and Z is preferably a fluorine atom.

Among the processes of the present invention, first of all, the process for producing a compound (2) from a compound (1) is described below. Reduction of the trans isomer of a compound (1) affords a piperidinecarbinol, a compound (2). This reaction is usually conducted in a reaction solvent.

As the reductant, a hydride reductant or a metal hydride reductant is preferred, and its suitable examples are lithium aluminum hydride, sodium borohydride, sodium cyanoborohydride, sodium trimethoxyborohydride, lithium tri(t-butoxy)aluminum hydride, sodium bis(2-methoxyethoxy)aluminum hydride, diisobutylaluminum hydride, alane, diborane and the like.

As the reaction solvent, any solvent that is not reducible itself may be used, and a saturated hydrocarbon solvent, an arene solvent and an etherial solvent are preferred. When sodium borohydride or its derivative is used as the reductant, an alcoholic solvent and a hydrous solvent are preferred.

Suitable examples of the reaction solvent are pentane, hexane, heptane, petroleum ether, cyclohexane, benzene, toluene, xylene, diethyl ether, tetrahydrofuran, 1,4-dioxane, 1,2-dimethoxyethane, diethylene glycol dimethyl ether, methanol, ethanol, 2-propanol, t-butanol, ethylene glycol, glycerine, methyl cellosolve, ethyl cellosolve and the like.

The reaction temperature in the process is preferably from 0 to 100° C., particularly preferably from 5 to 80° C. In the process, it is particularly preferred to conduct the reaction in an etherial solvent such as tetrahydrofuran by using lithium aluminum hydride as the reductant.

Next, the process for producing a compound (1') from a compound (3) is described. Reduction of the cyano group of a compound (3) and simultaneous intermolecular cyclization of the compound (3) afford a compound (1') wherein $R^1$ is a hydrogen atom. The reduction and cyclization is preferably conducted in the presence of a metallic catalyst by using hydrogen. The use of a metal catalyst and hydrogen allows the reaction to proceed at a relatively low pressure and improves selectivity. The reaction temperature is preferably from 5 to 100° C., particularly preferably from 25 to 60° C. The pressure is usually as low as less than 20 atm (gauge pressure), preferably from 1 to 5 atm, and particularly preferably from 1 to 3 atm.

The metallic catalyst may be any metallic catalyst commonly used for catalytic reduction, and for example, palladium, rhodium, ruthenium, nickel, platinum oxide, Raney cobalt or the like may be mentioned. Among them, a Raney nickel catalyst is particularly preferred because of its low price. This reaction is usually conducted in a reaction solvent. As the reaction solvent, the solvent which dissolves a compound (3) as the substrate and can not be hydrogenated is used. For example, ethers, halogen-substituted hydrocarbons, arenes, saturated hydrocarbons, alcohols, esters, acid anhydrides may be used.

Suitable examples of the reaction solvent are diethyl ether, t-butyl methyl ether, tetrahydrofuran, 1,4-dioxane, 1,2-dimethoxyethane, diethylene glycol dimethyl ether, dichloromethane, chloroform, 1,2-dichloroethane, toluene, xylene, pentane, hexane, heptane, octanol, decanol, dodecanol, ethyl acetate, methyl acetate, methyl propionate, acetic anhydride and the like. Among them, particularly preferred are lower alcohols such as methanol, ethanol, 1-propanol, 2-propanol, 1-butanol, 2-butanol, t-butanol, pentanol, hexanol, cyclohexanol, ethylene glycol, glycerine, methyl cellosolve, ethyl cellosolve and diethylene glycol. Lower alkanols such as methanol, ethanol, 2-propanol and t-butanol are most preferred.

Compounds (1) other than compounds (1') can be prepared from the corresponding compounds analogous to the compounds (3) by the same process as described above. The above mentioned hydrogenation with a metallic catalyst enables selective production of compounds (1) at a relatively low pressure even if X is not a halogen atom.

The compound (1) obtained by the above process is usually in the form of a mixture of the cis/trans isomers. Since the trans isomer is necessary for production of paroxetine, it is better to obtain the trans isomer only rather than the cis/trans isomers. For this purpose, the cis isomer may be converted into the trans isomer by utilizing the fact that a trans isomer is more stable than a cis isomer. In a preferred embodiment, the cis isomer is converted into the trans isomer by treating the isomer mixture with an appropriate base or acid in a solvent to obtain the trans isomer only. It is also possible to preferentially produce a trans isomer by conducting the above-mentioned process for producing a compound (1) from a compound (3) under relatively mild conditions (for example, at a relatively low reaction temperature).

As the base, alkali metal hydrides, alkaline earth metal hydrides, alkoxides, alkyl metals, metal amides, hydroxides, and amines are preferred. Suitable examples of the base are sodium hydride, potassium hydride, calcium hydride, sodium methoxide, sodium ethoxide, potassium t-butoxide, methyllithium, n-butyllithium, s-butyllithium, t-butyllithium, sodium amide, potassium amide, lithium diisopropylamide, sodium hydroxide, potassium hydroxide, calcium hydroxide, 1,8-diazabicyclo[5.4.0]undeca-7-ene (DBU), 1,5-diazabicyclo[4.3.0]nona-5-ene (DBN), 1,4-diazabicyclo[2.2.2]octane (DABCO) and the like.

As the solvent, saturated hydrocarbon solvents, arene solvents, etherial solvents, alcoholic solvents and polar solvents such as amides and sulfoxides are preferred. Preferred examples are pentane, hexane, heptane, cyclohexane, toluene, xylene, diethyl ether, t-butyl methyl ether, tetrahydrofuran, 1,4-dioxane, 1,2-dimethoxyethane, methanol, ethanol, 2-propanol, t-butanol, N,N-dimethylformamide, N,N-dimethylacetamide, dimethyl sulfoxide, N-methylpyrrolidinone, hexamethylphosphoramide and pyridine.

When an alkali metal hydride or an alkaline earth metal hydride is used as the base, a polar solvent such as N,N-dimethylformamide or a dimethyl sulfoxide is preferably used. When an amide or an alkyl metal is used as the base, a hydrocarbon solvent such as pentane, hexane, or an etherial solvent such as diethyl ether or tetrahydrofuran is preferred.

When an amine or a hydroxide is used as the base, an arene solvent such as toluene, an alcoholic solvent such as methanol or ethanol or a polar solvent such as dimethyl sulfoxide is preferred. When the base is an alkoxide, the corresponding alcohol is preferred. As the acid, a mineral acid or an organic acid is preferred, and its suitable examples are sulfuric acid, hydrochloric acid, phosphoric acid, p-toluenesulfonic acid, camphorsulfonic acid and the like.

When an acid is used, the solvent is preferably a saturated hydrocarbon solvent, an arene solvent, an etherial solvent, a halogen-substituted hydrocarbon solvent, an alcoholic solvent or an aqueous solvent. Suitable examples of the solvent are pentane, hexane, heptane, toluene, xylene, diethyl ether, t-butyl methyl ether, tetrahydrofuran, 1,4-dioxane, 1,2-dimethoxyethane, dichloromethane, chloroform, 1,2-dichloroethane, methanol, ethanol, 2-propanol, t-butanol, ethylene glycol, glycerine, methyl cellosolve, ethyl cellosolve and water.

When $R^1$ of a compounds (1) or (2) is a hydrogen atom, conversion of $R^1$ to a different substituent is not restricted to any particular processes. However, a compound (1) wherein $R^1$ is a hydrogen atom is preferably converted to a compound (1) wherein $R^1$ is a lower alkyl group or an aralkyl group by reacting with an alkylation agent in the presence of a base. In the case of a compound (2) wherein $R^1$ is a hydrogen atom, $R^1$ is preferably converted into a lower alkyl group or an aralkyl group by reacting with an aldehyde, a ketone or an equivalent thereof under a reducing atmosphere.

Examples of the base used for the above-mentioned conversion of $R^1$ of a compound (1) are sodium hydride, potassium hydride, potassium carbonate, sodium hydroxide, potassium hydroxide, an alkyllithium and the like. The alkylation agent used for the conversion is preferably a lower alkyl halide, a lower sulfonic acid ester or an aralkyl halide. Its suitable examples are iodomethane, iodoethane, bromoethane, dimethyl sulfate, diethyl sulfate, benzyl bromide and the like.

As the aldehyde used for the above-mentioned conversion of $R^1$ of a compound (2), acetaldehyde, formaldehyde, butyraldehyde, benzaldehyde or the like may be used, depending on the desired $R^1$. Likewise, as the ketone, acetone, diethyl ketone, benzophenone or the like may be use. As the equivalent of an aldehyde or a ketone, a corresponding acetal or an aldehyde oligomer (such as paraformaldehyde, 1,3,5-trioxane or a paraaldehyde) may be mentioned. When an acetal is used, an appropriate acid (such as hydrochloric acid, sulfuric acid, acetic acid, p-toluenesulfonic acid or trifluoroacetic acid) is preferably added. A compound (2) wherein $R^1$ is a secondary alkyl or aralkyl group is prepared by reacting a compound (2) wherein $R^1$ is a hydrogen atom with a ketone and then adding to the resulting iminium salt a nucleophilic agent such as an alkyl metal.

An ordinary reductant which reduces imine is enough for the reaction under a reducing atmosphere, and for example, hydrogen in the presence of a metallic catalyst, a hydride reductant such as sodium hydride or sodium cyanoborohydride, formic acid or its derivative may be used as the reductant. The reaction under a reducing atmosphere is preferably effected by hydrogenation with hydrogen in the presence of a metallic catalyst. In the hydrogenation, a metallic catalyst suitable for the above-mentioned reduction with hydrogen may be used. Likewise, a reaction solvent and reaction conditions as mentioned above may be used. The hydrogenation is most preferably conducted in the presence of a metal palladium catalyst or a Raney nickel catalyst supported on activated carbon at atmospheric pressure or under pressure. In the hydrogenation and reduction using sodium borohydride or the like as the reductant, an alcoholic solvent or a hydrous solvent is preferably used.

Suitable examples of the solvent are pentane, hexane, heptane, petroleum ether, cyclohexane, benzene, toluene, xylene, diethyl ether, tetrahydrofuran, 1,4-dioxane, 1,2-dimethoxyethane, diethylene glycol dimethyl ether, methanol, ethanol, 2-propanol, t-butanol, ethylene glycol, glycerine, methyl cellosolve, ethyl cellosolve and the like.

As the process for producing a compound (3), a process which comprises conjugate addition of a cyanoacetic acid ester to a cinnamic acid ester represented by the general formula (8) in the presence of a base is preferred:

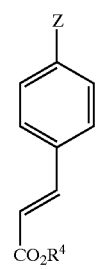

(8)

wherein $R^4$ is a hydrogen atom, a lower alkyl group, an aryl group or an aralkyl group, and Z is the same as defined for the general formula (3).

$R^4$ is preferably, though not necessarily, the same as $R^3$ of a compound (3), because ester exchange would be unnecessary. The base used for the reaction is preferably an alkali metal hydride, an alkaline earth metal hydride, an alkali metal hydroxide, an alkaline earth metal hydroxide, an alkali metal carbonate, an alkoxide, a metal amide, an alkyl metal or the like. Suitable examples of the base are lithium hydride, sodium hydride, potassium hydride, calcium hydride, sodium hydroxide, potassium hydroxide, calcium hydroxide, barium hydroxide, sodium carbonate, potassium carbonate, sodium methoxide, sodium ethoxide, potassium t-butoxide, sodium amide, potassium amide, lithium diisopropylamide, n-butyllithium, s-butyllithium, t-butyllithium and the like.

This reaction is usually carried out in a reaction solvent. As the reaction solvent, a saturated hydrocarbon solvent, an arene solvent, an etherial solvent, an alcoholic solvent or a polar solvent such as an amide or a sufoxide is preferred. As suitable examples of the reaction solvent, pentane, hexane, heptane, cyclohexane, toluene, xylene, diethyl ether, t-butyl methyl ether, tetrahydrofuran, 1,4-dioxane, 1,2-dimethoxyethane, methanol, ethanol, 2-propanol, t-butanol, N,N-dimethylformamide, N,N-dimethylacetamide, dimethyl sulfoxide, N-methyl-2-pyrrolidinone, hexamethylphosphoramide, pyridine and the like may be mentioned.

When the base is an alkali metal hydride or an alkaline earth metal hydride, a polar solvent such as N,N-dimethylformamide or dimethyl sulfoxide is preferably used as the reaction solvent. When the base is an amide or an alkyl metal, a hydrocarbon solvent such as pentane or hexane or an etherial solvent such as diethyl ether or tetrahydrofuran is preferred as the reaction solvent.

When the base is a carbonate or a hydroxide, an alcoholic solvent or a polar solvent is preferred as the reaction solvent. When the base is an alkoxide, the corresponding alcohol is preferred as the reaction solvent. In particular, use of an alcoholic reaction solvent and an alkoxide which have groups corresponding to $R^2$ and $R^3$ of the compound (3) is most preferred. For example, when $R^2$ and $R^3$ are ethyl groups, it is preferred to use ethoxide as the base in ethanol.

One of the main objects of the present invention is to provide a process for producing trans-4-(p-fluorophenyl)-1-methyl-3-piperidinecarbinol. trans-4-(p-Fluorophenyl)-1-methyl-3-piperidinecarbinol can be prepared from a p-fluorocinnamic acid ester as the starting material by combining the above-mentioned processes. As the process, a process which comprises the above-mentioned sequence of steps (i) to (v) is preferred. Details of each step are described above.

Now, the present invention is described in further detail with reference to Examples, but it should be understood that the present invention is by no means restricted to these specific examples.

EXAMPLE 1

To 12 g of ethyl cyanoacetate dissolved in 20 mL of ethanol, 8 g of sodium ethoxide and 40 mL of ethanol were added under cooling with ice, and then 20 g of ethyl p-fluorocinnamate and 40 mL of ethanol were added. The reaction mixture was heated under reflux for 20 hours and then filtered. The filtrate was poured into a mixture of 200 g of ice and 10 mL of concentrated hydrochloric acid and extracted with chloroform. The extract was concentrated and separated by silica gel column chromatography (hexane: ethyl acetate=9:1) to obtain 15 g of diethyl 2-cyano-3-(p-fluorophenyl)glutarate as a diastereomer mixture.

$^1$H NMR(400 MHz, CDCl$_3$) δ 7.27–7.33 (m, 2H); 7.01–7.06 (m, 2H); 4.1–4.2 (m, 4H); 3.78–4.01 (m, 2H); 2.81–3.03 (m, 2H) 1.13–1.23; (m, 6H). $^{19}$F NMR(376 MHz, CDCl$_3$, CFCl$_3$=0 ppm constant hereinafter) δ–113.9;–114.0.

EXAMPLE 2

12.9 g of ethyl cyanoacetate dissolved in 18 mL of N,N-dimethylformamide was added dropwise to a mixture of 4.5 g of sodium hydride and 40 mL of N,N-dimethylformamide under cooling with ice, and after 1.5 hours of stirring at room temperature, a solution of 20 g of ethyl p-fluorocinnamate in 18 mL of N,N-dimethylformamide was added. The mixture was heated at 50 to 60° C. for 21 hours. 30 mL of absolute ethanol was added under cooling with ice, and then an ethanol solution of acetic acid was added. After addition of water, the reaction mixture was extracted with ethyl acetate, and the extract was dried, concentrated and separated by silica gel column chromatography (hexane: ethyl acetate=5:1) to obtain 23.9 g of diethyl 2-cyano-3-(p-fluorophenyl)glutarate as a diastereomer mixture.

EXAMPLE 3

To 1 g of ethyl cyanoacetate dissolved in 5 mL of N,N-dimethylformamide, 0.5 g of sodium hydride was added under cooling with ice, and after stirring at room temperature for 30 minutes, 1.5 g of ethyl p-fluorophenylcinnamate was added. The reaction mixture was stirred at room temperature for 4 hours. After addition of ethanol under cooling with ice, the reaction mixture was poured into iced water and extracted with a solvent mixture of hexane and ethyl acetate. The extract was washed with water, and dried and concentrated. The resulting oily substance was separated by silica gel column chromatography (hexane: ethyl acetate=9:1) to obtain 1.8 g of diethyl 2-cyano-3-(p-fluorophenyl)glutarate as a diastereomer mixture.

EXAMPLE 4

5 g of diethyl 2-cyano-3-(p-fluorophenyl)glutarate obtained in Examples 1 to 3 was put into a mixture of 1 g of a commercially available developed Raney nickel and 110 mL of ethanol, and the resulting reaction mixture was heated at 50° C. for 6 hours under a pressure of 3 atm (gauge pressure) of hydrogen and then filtered through celite. The filtrate was concentrated, and addition of ethyl acetate to the resulting oily substance was followed by concentration. Then, hexane was added to obtain 3.3 g of a cis/trans mixture of ethyl 4-(p-fluorophenyl)-6-oxo-3-piperidinecarboxylate as a crystalline white powder.

$^1$H NMR(400 MHz, CDCl$_3$) δ 7.12–7.20 (m, 2H); 6.98–7.04 (m, 2H); 6.48 (brs, 1H); 3.9–4.1 (m, 2H); 3.3–3.8 (m, 3H); 2.5–3.1 (m, 3H); 0.97–1.21; (m, 3H). $^{19}$F NMR (376 MHz, CDCl$_3$) δ–115.3;–115.5.

EXAMPLE 5

10 g of diethyl 2-cyano-3-(p-fluorophenyl)glutarate obtained in Examples 1 to 3 was added to a mixture of 2.8 g of a commercially available developed Raney nickel and 120 mL of methanol, and the reaction mixture was heated at 60° C. for 5 hours under a pressure of 2.5 atm (gauge pressure) of hydrogen. The reaction mixture was filtered through celite, and the filtrate was concentrated. The resulting oily substance was recrystallized to obtain 7.4 g of a cis/trans mixture of ethyl 4-(p-fluorophenyl)-6-oxo-3-piperidinecarboxylate as a crystalline white powder.

EXAMPLE 6

5 g of diethyl 2-cyano-3-(p-fluorophenyl)glutarate obtained in Examples 1 to 3 was added to a mixture of 1.4 g of a commercially available developed Raney nickel and 120 mL of 2-propanol, and the reaction mixture was heated at 50° C. for 2.5 hours under a pressure of 2.5 atm (gauge pressure) of hydrogen. The reaction mixture was filtered through Celite, and the filtrate was concentrated. The resulting oily substance was recrystallized to obtain 3.4 g of a cis/trans mixture of ethyl 4-(p-fluorophenyl)-6-oxo-3-piperidinecarboxylate as a crystalline white powder.

EXAMPLE 7

5 g of diethyl 2-cyano-3-(p-fluorophenyl)glutarate obtained in Examples 1 to 3 was added to a mixture of 1.4 g of a commercially available developed Raney nickel and 120 mL of ethanol, and the reaction mixture was allowed to react at 27° C. for 6 hours under a hydrogen pressure of 2.5 atm (gauge pressure) of hydrogen. The reaction mixture was filtered through Celite, and the filtrate was concentrated. The resulting oily substance was recrystallized to obtain 2 g of ethyl trans-4-(p-fluorophenyl)-6-oxo-3-piperidinecarboxylate as a crystalline white powder.

$^1$H NMR(400 MHz, CDCl$_3$) δ 7.17–7.20 (m, 2H); 7.00–7.05 (m, 2H); 6.04 (brs, 1H); 3.91–3.98 (m, 2H); 3.64 (dd, J=10,11 Hz, 1H); 3.50–3.55 (m, 1H); 3.36–3.43 (m, 1H); 2.93–2.99 (m, 1H); 2.74 (dd, J=6,18 Hz, 1H); 2.55 (dd, J=11,18 Hz, 1H); 0.99 (t, J=7 Hz, 3H). $^{19}$F NMR(376 MHz, CDCl$_3$) δ–115.3.

EXAMPLE 8

0.1 g of the cis/trans mixture of ethyl 4-(p-fluorophenyl)-6-oxo-3-piperidinecarboxylate obtained in Examples 4 to 6 was added to 10 mL of toluene, and 26 mg of sodium ethoxide was added. The reaction mixture was heated at 90° C. for 5 hours, then poured into ice water, and extracted with ethyl acetate. The extract was washed with water, dried and concentrated to obtain 50 mg of ethyl trans-4-(p-fluorophenyl)-6-oxo-3-piperidinecarboxylate.

EXAMPLE 9

3.8 g of the cis/trans mixture of ethyl 4-(p-fluorophenyl)-6-oxo-3-piperidinecarboxylate obtained in Examples 4 to 6 was added to 100 mL of toluene, and 2.7 mL of a 28% methanol solution of sodium methoxide was added. The reaction mixture was heated at 110° C. for 2.5 hours, then poured into ice water and extracted with ethyl acetate. The extract was washed with water, dried and concentrated to obtain 3.28 g of ethyl trans-4-(p-fluorophenyl)-6-oxo-3-piperidinecarboxylate.

EXAMPLE 10

A solution of 1 g of ethyl trans-4-(p-fluorophenyl)-6-oxo-3-piperidinecarboxylate obtained in Examples 7 to 9 in 15 mL of tetrahydrofuran was added dropwise to a mixture of 0.3 g of lithium aluminum hydride and 15 mL of dehydrated tetrahydrofuran under cooling with ice. The reaction mixture was stirred at room temperature for 2 hours and then heated at 50° C. for 17 hours. To the reaction mixture, ethyl acetate and then water were added dropwise under cooling with ice, and lastly 1 mL of a 10 N sodium hydroxide aqueous solution and 5 mL of water were added. Then the reaction mixture was stirred at room temperature for 1 hour and filtered through Celite. The filtrate was dried, concentrated and separated by column chromatography to obtain 0.52 g of trans-4-(p-fluorophenyl)-3-piperidinecarbinol as crystals.

$^1$H NMR(400 MHz, CDCl$_3$) δ 7.15–7.19 (m, 2H); 6.97–7.01 (m, 2H); 3.43–3.41 (m, 2H); 3.21–3.26 (m, 1H); 3.12–3.17 (m, 1H); 2.66–2.72 (m, 1H); 2.60 (t, J=11 Hz, 1H); 2.42 (m, 1H); 1.65–1.86 (m, 3H); 1.55 (s). $^{19}$F NMR (376 MHz, CDCl$_3$) δ–117.2.

EXAMPLE 11

A solution of 1.69 g of ethyl trans-4-(p-fluorophenyl)-6-oxo-3-piperidinecarboxylate obtained in Examples 7 to 9 in 40 mL of dehydrated tetrahydrofuran was added dropwise to a mixture of 408.8 mg of lithium aluminum hydride and 20 mL of dehydrated tetrahydrofuran under cooling with ice. The reaction mixture was stirred until it warmed to room temperature, and then refluxed under heating for 8 hours. To the reaction mixture, 30 mL of diethyl ether was added, and then 1.4 mL of a sodium hydrogen carbonate aqueous solution was added dropwise under cooling with ice. The mixture was stirred at room temperature for 1 hour and filtered through Celite. The filtrate was dried and concentrated to obtain 1.33 g of trans-4-(p-fluorophenyl)-3-piperidinecarbinol as crystals.

EXAMPLE 12

0.1 g of trans-4-(p-fluorophenyl)-3-piperidinecarbinol obtained in Examples 10 and 11 was added to a mixture of 30 mg of 5% palladium-supporting activated carbon, 1 mL of water and 1 mL of formalin. After addition of 5 mL of ethanol, the reaction mixture was stirred and subjected to hydrogenation for 2 hours at room temperature at atmospheric pressure. The mixture was filtered through Celite, and the filtrate was concentrated, then diluted with water and extracted with chloroform. The organic layer as obtained was concentrated, and after addition of toluene, concentrated again. The precipitated was recrystallized in hexane and collected by filtration to obtain 83 mg of trans-4-(p-fluorophenyl)-1-methyl-3-piperidinecarbinol.

$^1$H NMR(400 MHz, CDCl$_3$) δ 7.15–7.19 (m, 2H); 6.97–7.01 (m, 2H); 3.41 (dd, J=3,11 Hz, 1H); 3.24 (dd, J=6,11 Hz, 1H); 3.19 (d, J=11 Hz, 1H); 2.99 (d, J=11 Hz, 1H); 2.38 (s, 3H); 2.34 (m, 1H); 1.79–2.08 (m, 5H); 1.19 (brs, 1H). $^{19}$F NMR(376 MHz, CDCl$_3$) δ–117.0.

EXAMPLE 13

3 g of trans-4-(p-fluorophenyl)-3-piperidinecarbinol obtained in Examples 10 and 11 was added to a mixture of 1 g of a commercially available developed Raney nickel and 15 mL of formalin, and 105 mL of methanol was added with stirring. Then the reaction mixture was heated at a temperature of from 50 to 60° C. for 4 hours under a pressure of 2.5 atm (gauge pressure) of hydrogen for hydrogenation. The reaction mixture was filtered through celite, and the filtrate was concentrated, then diluted with water and extracted with chloroform. The organic layer thus obtained was concentrated, and after addition of toluene, concentrated again. The precipitate was recrystallized in hexane and collected by filtration to obtain 2.9 g of trans-4-(p-fluorophenyl)-1-methyl-3-piperidinecarbinol.

According to the present invention, it is possible to efficiently and readily produce an 4-aryl-3-piperidinecarbinol useful as an intermediate for synthesizing of medicines (such as paroxetine) from a cheap and readily available cyanoacetic acid derivative and a cinnamic acid derivative.

What is claimed is:

1. A process for producing a piperidinecarbinol represented by formula (2), which comprises reducing the trans isomer of a compound represented by formula (1):

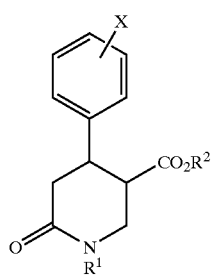

(1)

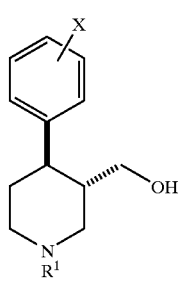

(2)

wherein X is a fluorine atom at the p-position, $R^1$ is a hydrogen atom, a methyl group or a benzyl group, and $R^2$ is a hydrogen atom or a lower alkyl group.

2. A process for producing a piperidinecarbinol represented by formula (2), which comprises reducing the trans isomer of a compound represented by formula (1):

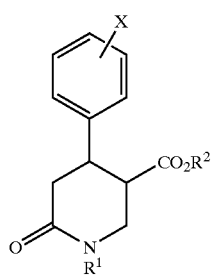

(1)

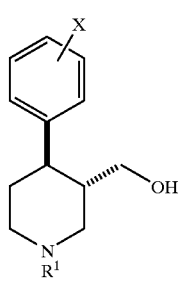

(2)

wherein the trans isomer of the compound represented by formula (1) is a lower alkyl trans-4-(p-fluorophenyl)-6-oxo-3-piperidinecarboxylate, and the piperidinecarbinol represented by formula (2) is trans-4-(p-fluorophenyl)-3-piperidinecarbinol.

3. A process for producing a compound represented by formula (1') wherein $R^1$ is a hydrogen atom, which comprises reduction of the cyano group of a cyanoglutaric acid compound by formula (3) and the simultaneous intramolecular cyclization of the cyanoglutaric acid compound:

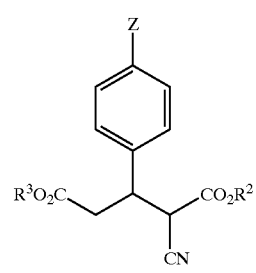

(3)

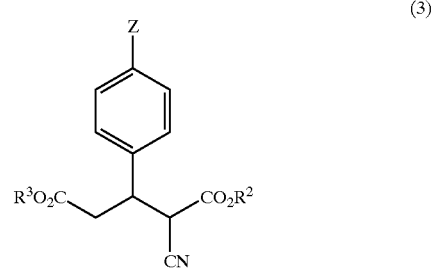

(1')

wherein Z is a fluorine atom, and each of $R^2$ and $R^3$ is a hydrogen atom or a lower alkyl group.

4. A process for producing a compound represented by formula (1') wherein $R^1$ is a hydrogen atom, which comprises reduction of the cyano group of a cyanoglutaric acid compound by formula (3) and the simultaneous intranolocular cyclization of the cyanoglutaric acid compound:

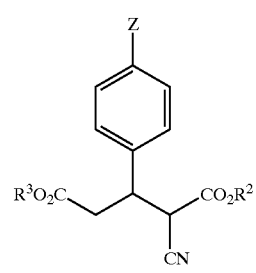

(3)

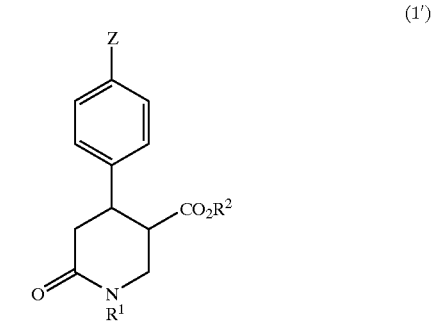

(1')

wherein the cyanoglutaric acid compound represented by formula (3) is a di-lower-alkyl 2-cyano-3-(p-fluorophenyl)glutarate, and the compound represented by formula (1') wherein $R^1$ is a hydrogen atom is a lower alkyl 4-(p-fluorophenyl)-6-oxo-3-piperidinecarboxylate.

5. A process for producing a compound represented by formula (1') wherein $R^1$ is a hydrogen atom, which comprises reduction of the cyano group of a cyanoglutaric acid compound by formula (3) and the simultaneous intramolecular cyclization of the cyanoglutaric acid compound:

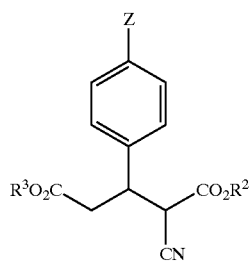

(3)

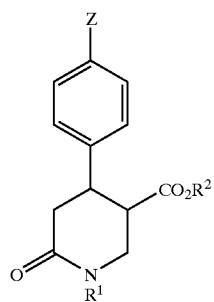

(1')

wherein each of $R^2$ and $R^3$ is a hydrogen atom, a lower alkyl group, an aryl group or an aralkyl group, and Z is a halogen atom, and wherein the reaction is carried out at a pressure of 20 atm or less in the presence of a metallic catalyst using hydrogen as a reductant.

6. A process for producing trans-4-(p-fluorophenyl)-1-methyl-3-piperidinecarbinol, which comprises the following sequence of steps (i) to (v):

(i) a step of conjugately adding a cyanoacetic acid ester to a p-fluorocinnamic acid ester to prepare a 2-cyano-3-(p-fluorophenyl)glutaric acid diester;

(ii) a step of hydrogenating the 2-cyano-3-(p-fluorophenyl)glutaric acid diester in the presence of a metallic catalyst to prepare a cis/trans mixture of a 4-(p-fluorophenyl)-6-oxo-3-piperidinecarboxylic acid ester;

(iii) a step of treating the cis/trans mixture with a base or an acid to prepare a trans-4-(p-fluorophenyl)-6-oxo-3-piperidinecarboxylic acid ester;

(iv) a step of reducing the trans-4-(p-fluorophenyl)-6-oxo-3-piperidinecarboxylic acid ester to trans-4-(p-fluorophenyl)-3-piperidinecarbinol; and (v) a step of reacting the trans-4-(p-fluorophenyl)-3-piperidinecarbinol with formaldehyde or paraformaldehyde under a reductive atmosphere to prepare trans-4-(p-fluorophenyl)-1-methyl-3-piperidinecarbinol.

7. The process according to claim 1, wherein $R^1$ is a hydrogen atom.

8. The process according to claim 1, wherein $R^1$ is a methyl group.

9. The process according to claim 1, wherein $R^1$ is a benzyl group.

10. The process according to claim 1, wherein $R^2$ is a hydrogen atom.

11. The process according to claim 1, wherein $R^2$ is a lower alkyl group.

12. The process according to claim 1, wherein each of $R^1$ and $R^2$ is a hydrogen atom.

13. The process according to claim 3, wherein each of $R^2$ and $R^3$ is a hydrogen atom.

14. The process according to claim 3, wherein each of $R^2$ and $R^3$ is a lower alkyl group.

15. The process according to claim 5, wherein each of $R^2$ and $R^3$ is a hydrogen atom.

16. The process according to claim 5, wherein each of $R^2$ and $R^3$ is a lower alkyl group.

17. The process according to claim 6, wherein in (iii) the cis/trans mixture is treated with the base.

18. The process according to claim 6, wherein in (iii) the cis/trans mixture is treated with the acid.

* * * * *